(12) United States Patent
Ke et al.

(10) Patent No.: US 6,352,970 B1
(45) Date of Patent: Mar. 5, 2002

(54) TREATMENT OF SKELETAL DISORDERS

(75) Inventors: HuaZhu Ke, Ledyard; Claire M. Steppan, New London; Andrew Gordon Swick, East Lyme, all of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/253,329

(22) Filed: Feb. 19, 1999

Related U.S. Application Data

(60) Provisional application No. 60/075,491, filed on Feb. 23, 1998.

(51) Int. Cl.[7] .................. A61K 38/00; A61K 31/66; A61K 31/56
(52) U.S. Cl. ................ 514/2; 514/108; 514/109; 514/182
(58) Field of Search ............... 514/109, 108, 514/2, 182

(56) References Cited

FOREIGN PATENT DOCUMENTS

| GB | 2292382 | 8/1995 | ........... C07K/14/47 |
|---|---|---|---|
| WO | 9732022 | 4/1997 | ........... C12N/15/16 |
| WO | 9718833 | 5/1997 | .......... A61K/38/22 |
| WO | WO9731640 | 9/1997 | |
| WO | WO9739767 | 10/1997 | |
| WO | WO9953939 | 10/1999 | |

OTHER PUBLICATIONS

Halaas et al., Science 269:543–546, 1995.
Tartaglia et al., Cell 83:1263–1271, 1995.
Liu et al., Americal Society for Bone and Mineral Research, 19th Annual Meeting, Sep. 10–14, 1997, Cincinati Ohio.

*Primary Examiner*—Theodore J. Criares
(74) *Attorney, Agent, or Firm*—Peter C. Richardson; Gregg C. Benson; Michelle A. Sherwood

(57) ABSTRACT

This invention relates to methods for treating bone loss in a mammal by administering to the mammal a therapeutically effective amount of leptin or a leptin mimetic. This invention also relates to methods for treating bone fracture, enhancing bone healing following facial reconstruction, maxillary reconstruction or madibular reconstruction, enhancing long bone extension, enhancing the healing rate of a bone graft, enhancing prosthetic growth and inducing vertebral synostosis by administering a therapeutically effective amount of leptin or a leptin mimetic. This invention further relates to methods and compositions comprising leptin or a leptin mimetic and estrogen, a selective estrogen receptor modulator or a bisphonate for treating the above-recited diseases and conditions.

17 Claims, No Drawings

TREATMENT OF SKELETAL DISORDERS

This Application claims benefit of Prov. No. 60/075,491 filed Feb. 23, 1998.

BACKGROUND OF INVENTION

This invention relates to the use of leptin and leptin mimetics to augment bone mass including the prevention and treatment of skeletal disorders such as osteoporosis in vertebrates, e.g., mammals, including humans.

Osteoporosis is a systemic skeletal disorder, characterized by low bone mass and deterioration of bone tissue, with a consequent increase in bone fragility and susceptibility to fracture. In the U.S., the condition affects more than 25 million people and causes more than 1.3 million fractures each year, including 500,000 spine, 250,000 hip and 240,000 wrist fractures annually. Hip fractures are the most serious, with 5–20% of patients dying within one year, and over 50% of survivors being incapacitated.

The elderly are at greatest risk of osteoporosis, and the problem is therefore predicted to increase significantly with the aging of the population. Worldwide fracture incidence is forecast to increase three-fold over the next 60 years, and one study estimates that there will be 4.5 million hip fractures worldwide in 2050.

Women are at greater risk of osteoporosis than men. Women experience a sharp acceleration of bone loss during the five years following menopause. Other factors that increase the risk include smoking, alcohol abuse, a sedentary lifestyle and low calcium intake.

In addition to hip fractures numbering approximately 250,000/year in the U.S., approximately, 20–25 million women and an increasing number of men have detectable vertebral fractures. Hip fracture is associated with a 12% mortality rate within the first two years and with a 30% rate of patients requiring nursing home care after the fracture. While this is already significant, the economic and medical consequences of convalescence due to slow or imperfect healing of these bone fractures is expected to increase, due to the aging of the general population.

There are currently two main types of pharmaceutical therapy for the treatment of osteoporosis and skeletal fractures. The first is the use of anti-resorptive compounds to inhibit the resorption of bone tissue and therefore prevent bone loss and reduce the incidence of skeletal fractures.

Estrogen is an example of an anti-resorptive agent. It is known that estrogen prevents post-menopausal bone loss and reduces skeletal fractures. However, estrogen fails to restore bone to the established osteoporotic skeleton. Furthermore, long-term estrogen therapy, however, has been implicated in a variety of disorders, including an increase in the risk of uterine cancer, endometrial cancer and possibly breast cancer, causing many women to avoid this treatment. The significant undesirable effects associated with estrogen therapy support the need to develop alternative therapies for osteoporosis.

A second type of pharmaceutical therapy for the treatment of osteoporosis and bone fractures is the use of anabolic agents to promote bone formation and increase bone mass. This class of agents is expected to restore bone to the established osteoporotic skeleton by stimulating osteoblastic bone formation. Currently, such pharmaceutical therapy is not available for established osteoporotic patents.

Leptin, a product of the obese gene, is a 16 kDa protein. Leptin is produced by mature adipocytes and is secreted in plasma. Leptin has been reported to increase lean body mass (Friedman et al., UK Patent Application No. GB 2292382 and Pelleymounter et al., International Patent Application Publication Number WO97/18833) and decrease fat body mass (Halaas et al., Science 269:543–546, 1995). Further, a leptin receptor, OB-R, has been identified and cloned (Tartaglia et al., Cell 83:1263–1271, 1995). Further, leptin has been disclosed to stimulate cortical bone formation in ob/ob mice (Liu et al., Americal Society for Bone and Mineral Research, 19th Annual Meeting, Sep. 10–14, 1997, Cincinati, Ohio).

Skeletal disorders are highly prevalent diseases caused by nutrition deficiency, sex steroid deficiency, aging, trauma or other factors. All approved therapies and clinically advanced candidates including calcitonin, estrogen replacement therapy, bisphosphonates and tissue selective estrogen agonists act to prevent bone loss by inhibiting bone resorption, but these agents cannot restore bone mass. Thus, there is significant medical need for agents that would increase bone mass and strength above a critical threshold in established osteoporotic patients, fractured patients, and other skeletal disorder patients.

SUMMARY OF THE INVENTION

This invention is directed to methods for augmenting bone mass and preventing bone loss in a vertebrate, e.g., a mammal (including humans) comprising administering to said vertebrate, e.g., a mammal, a therapeutically effective amount of leptin or a leptin mimetic.

This invention is also directed to methods for treating a vertebrate, e.g. a mammal (including a human being) having a condition which presents with low bone mass comprising administering to said vertebrate, e.g., mammal, having a condition which presents with low bone mass a therapeutically effective amount of leptin or a leptin mimetic.

Yet another aspect of this invention is directed to methods for treating osteoporosis, bone fractures, osteotomy, bone loss associated with periodontitis, prosthetic ingrowth, or inducing vertebral synostosis in a vertebrate, e.g. a mammal (including a human being) by administering to said vertebrate, e.g., mammal, suffering from or susceptible to osteoporosis, bone fractures, osteotomy, bone loss associated with periodontitis, prosthetic ingrowth or vertebral synostosis a therapeutically effective amount of leptin or a leptin mimetic.

Yet another aspect of this invention is directed to methods for treating osteoporosis in a vertebrate, e.g., a mammal (including a human being), by administering to said vertebrate, e.g., mammal, suffering from or susceptible to osteoporosis a therapeutically effective amount of a leptin or a leptin mimetic.

Yet another aspect of this invention is directed to methods for treating osteotomy bone loss in a vertebrate, e.g., a mammal (including a human being), by administering to said vertebrate, e.g., a mammal, suffering from or susceptible to an osteotomy bone loss a therapeutically effective amount of leptin or a leptin mimetic.

Yet another aspect of this invention is directed to methods for treating alveolar bone loss in a vertebrate, e.g., a mammal (including a human being), by administering to said vertebrate, e.g., mammal, suffering from or susceptible to an alveolar bone loss a therapeutically effective amount of leptin or a leptin mimetic.

Yet another aspect of this invention is directed to methods for treating bone loss associated with periodontitis in a vertebrate, e.g., a mammal (including a human being) by administering to said vertebrate, suffering from or susceptible to bone loss associated with periodontitis a therapeutically effective amount of leptin or a leptin mimetic.

Yet another aspect of this invention is directed to methods for treating childhood idiopathic bone loss in a child by administering to a child suffering from or susceptible to childhood idiopathic bone loss a therapeutically effective amount of leptin or a leptin mimetic.

Yet another aspect of this invention is directed to methods for treating "secondary osteoporosis", which includes glucocorticoid-induced osteoporosis, hyperthyroidism-induced osteoporosis, immobilization-induced osteoporosis, heparin-induced osteoporosis or immunosuppressive-induced osteoporosis in a vertebrate, e.g., a mammal (including a human being), by administering to said vertebrate, suffering from or susceptible to "secondary osteoporosis" a therapeutically effective amount of leptin or a leptin mimetic.

Yet another aspect of this invention is directed to methods for treating glucocorticoid-induced osteoporosis in a vertebrate, e.g., a mammal (including a human being), by administering to said vertebrate, suffering from or susceptible to glucocorticoid-induced osteoporosis a therapeutically effective amount of leptin or a leptin mimetic.

Yet another aspect of this invention is directed to methods for treating hyperthyroidism-induced osteoporosis in a vertebrate, e.g., a mammal (including a human being), by administering to said vertebrate, .e.g, mammal, suffering from or susceptible to hyperthyroidism-induced osteoporosis a therapeutically effective amount of leptin or a leptin mimetic.

Yet another aspect of this invention is directed to methods for treating immobilization-induced osteoporosis in a vertebrate, e.g., a mammal, (including a human being), by administering to said vertebrate, suffering from or susceptible to immobilization-induced osteoporosis a therapeutically effective amount of leptin or a leptin mimetic.

Yet another aspect of this invention is directed to methods for treating heparin-induced osteoporosis in a vertebrate, e.g., mammal, (including a human being), by administering to said vertebrate, e.g., a mammal suffering from or susceptible to heparin-induced osteoporosis a therapeutically effective amount of leptin or a leptin mimetic.

Yet another aspect of this invention is directed to methods for treating immunosuppressive-induced osteoporosis in a vertebrate, e.g., a mammal (including a human being), by administering to said vertebrate, e.g., mammal, suffering from or susceptible to immunosuppressive-induced osteoporosis a therapeutically effective amount of a leptin or a leptin mimetic.

Yet another aspect of this invention is directed to methods for enhancing bone fracture healing in a vertebrate, e.g., a mammal (including a human being), by administering to said vertebrate, suffering from or susceptible to a bone fracture a therapeutically effective amount of a leptin or leptin mimetic. In one aspect of this invention, leptin or a leptin mimetic is applied locally to the site of bone fracture.

Yet another aspect of this invention is directed to methods for enhancing bone healing following facial reconstruction or maxillary reconstruction or mandibular reconstruction in a vertebrate, e.g., a mammal (including a human being), by administering to said vertebrate, which has undergone facial reconstruction or maxillary reconstruction or mandibular reconstruction a therapeutically effective amount of leptin or a leptin mimetic. In one aspect of this invention, leptin or a leptin mimetic is applied locally to the site of bone reconstruction.

Yet another aspect of this invention is directed to methods for enhancing prosthetic ingrowth in a vertebrate, e.g., a mammal (including a human being), by administering to said vertebrate, in need of enhancing prosthetic ingrowth a therapeutically effective amount of leptin or a leptin mimetic.

Yet another aspect of this invention is directed to methods for inducing vertebral synostosis in a vertebrate, e.g., a mammal (including a human being), by administering to said vertebrate, undergoing surgery for vertebral synostosis a therapeutically effective amount of leptin or a leptin mimetic.

Yet another aspect of this invention is directed to methods for enhancing long bone extension in a vertebrate, e.g.,, a mammal (including a human being), by administering to said vertebrate, suffering from or susceptible to an insufficiently sized long bone a therapeutically effective amount of leptin or a leptin mimetic.

Yet another aspect of this invention is directed to methods for treating a bone graft in a vertebrate, e.g., a mammal (including a human being), by administering to said vertebrate, e.g., a mammal, suffering from or susceptible to a bone graft a therapeutically effective amount of leptin or a leptin mimetic. In one aspect of this invention, leptin or a leptin mimetic is applied locally to the site of the bone graft.

Yet another aspect of this invention is directed to methods for treating low bone mass or bone fracture in a vertebrate, e.g., a mammal (including a human being), comprising administering to said vertebrate, a therapeutically effective amount of leptin or a leptin mimetic, and estrogen.

Yet another aspect of this invention is directed to methods for treating low bone mass or bone fracture in a vertebrate, e.g., a mammal (including a human being), comprising administering to said vertebrate, a therapeutically effective amount of a leptin or a leptin mimetic, and a selective estrogen receptor modulator.

Preferred selective estrogen receptor modulators include droloxifene, raloxifene, tamoxifen; 4-hydroxy-tamoxifen; toremifene; centchroman; levormeloxifene; idoxifene; 6-(4-hydroxy-phenyl)-5-(4-(2-piperidin-1-yl-ethoxy)-benzyl)-naphthalen-2-ol; (4-(2-(2-aza-bicyclo[2.2.1]hept-2-yl)-ethoxy)-phenyl)-(6-hydroxy-2-(4-hydroxy-phenyl)-benzo[b]thiophen-3-yl)-methanone;

3-(4-(1,2-diphenyl-but-1-enyl)-phenyl)-acrylic acid;

2-(4-methoxy-phenyl)-3-[4-(2-piperidin-1-yl-ethoxy)-phenoxy]-benzo[b]thiophen-6-ol;

cis-6-(4-fluoro-phenyl)-5-(4-(2-piperidin-1-yl-ethoxy)-phenyl)-5,6,7,8-tetrahydro-naphthalene-2-ol;

(−)-cis-6-phenyl-5-(4-(2-pyrrolidin-1-yl-ethoxy)-phenyl)-5,6,7,8-tetrahydronaphthalene-2-ol;

cis-6-phenyl-5-(4-(2-pyrrolidin-1-yl-ethoxy)-phenyl)-5,6,7,8-tetrahydronaphthalene-2-ol;

cis-1-(6'-pyrrolodinoethoxy-3'-pyridyl)-2-phenyl-6-hydroxy-1,2,3,4-tetrahydronaphthalene;

1-(4'-pyrrolidinoethoxyphenyl)-2-(4"-fluorophenyl)-6-hydroxy-1,2,3,4-tetrahydroisoquinoline;

cis-6-(4-hydroxyphenyl)-5-(4-(2-piperidin-1-yl-ethoxy)-phenyl)-5,6,7,8-tetrahydro-naphthalene-2-ol;

1-(4'-pyrrolidinolethoxyphenyl)-2-phenyl-6-hydroxy-1,2,3,4-tetrahydroisoquinoline; and the pharmaceutically acceptable salts thereof.

Especially preferred selective estrogen receptor modulators include raloxifene; droloxifene; idoxifene;

3-(4-(1,2-diphenyl-but-1-enyl)-phenyl)-acrylic acid;

2-(4-methoxy-phenyl)-3-[4-(2-piperidin-1-yl-ethoxy)-phenoxy]-benzo[b]thiophen-6-ol;

cis-6-(4-fluoro-phenyl)-5-(4-(2-piperidin-1-yl-ethoxy)-phenyl)-5,6,7,8-tetrahydro-naphthalene-2-ol;

(−)-cis-6-phenyl-5-(4-(2-pyrrolidin-1-yl-ethoxy)-phenyl)-5,6,7,8-tetrahydronaphthalene-2-ol;

cis-6-phenyl-5-(4-(2-pyrrolidin-1-yl-ethoxy)-phenyl)-5,6,7,8-tetrahydronaphthalene-2-ol;

cis-1-(6'-pyrrolodinoethoxy-3'-pyridyl)-2-phenyl-6-hydroxy-1,2,3,4-tetrahydronaphthalene;

1-(4'-pyrrolidinoethoxyphenyl)-2-(4"-fluorophenyl)-6-hydroxy-1,2,3,4-tetrahydroisoquinoline;

cis-6-(4-hydroxyphenyl)-5-(4-(2-piperidin-1-yl-ethoxy)-phenyl)-5,6,7,8-tetrahydro-naphthalene-2-ol;

1-(4'-pyrrolidinolethoxyphenyl)-2-phenyl-6-hydroxy-1,2,3,4-tetrahydroisoquinoline; and the pharmaceutically acceptable salts thereof.

Still more especially preferred selective estrogen receptor modulators include raloxifene, droloxifene, idoxifene and (−)-cis-6-phenyl-5-(4-(2-pyrrolidin-1-yl-ethoxy)phenyl)-5,6,7,8-tetrahydronaphthalen-2-ol.

Yet another aspect of this invention is directed to methods for treating low bone mass or bone fracture in a vertebrate, e.g., a mammal (including a human being), comprising administering to said vertebrate, a therapeutically effective amount of leptin or a leptin mimetic, and a bisphosphonate.

Preferred bisphosphonates include tiludronic acid, alendronic acid, zoledronic acid, ibandronic acid, risedronic acid, etidronic acid, clodronic acid, and pamidronic acid and their pharmaceutically acceptable salts. Those skilled in the art will know that these compounds are often referred to as their ion form, e.g., tiludronate, alendronate, zoledronate, ibandronate, risedronate, etidronate, clodronate and pamidronate.

Especially preferred bisphosphonates include alendronate and risedroate.

Yet another aspect of this invention is directed to methods for enhancing bone healing following facial reconstruction, maxillary reconstruction, mandibular reconstruction, enhancing long bone extension, enhancing the healing rate of a bone graft, enhancing prosthetic ingrowth or inducing vertebral synostosis in a vertebrate, e.g., a mammal (including a human being), comprising administering to said vertebrate, a therapeutically effective amount of leptin or a leptin mimetic, and estrogen.

Yet another aspect of this invention is directed to methods for enhancing bone healing following facial reconstruction, maxillary reconstruction, mandibular reconstruction, enhancing long bone extension, enhancing the healing rate of a bone graft, enhancing prosthetic ingrowth or inducing vertebral synostosis in a vertebrate, e.g., a mammal (including a human being), comprising administering to said vertebrate, a therapeutically effective amount of leptin or a leptin mimetic, and a selective estrogen receptor modulator.

Yet another aspect of this invention is directed to methods for enhancing bone healing following facial reconstruction, maxillary reconstruction, mandibular reconstruction, enhancing long bone extension, enhancing the healing rate of a bone graft, enhancing prosthetic ingrowth or inducing vertebral synostosis in a vertebrate, e.g., a mammal (including a human being), comprising administering to said vertebrate, a therapeutically effective amount of leptin or a leptin mimetic, and a bisphosphonate.

Yet another aspect of this invention is directed to a pharmaceutical composition comprising a leptin mimetic and a pharmaceutically acceptable carrier or diluent.

Yet another aspect of this invention is directed to a pharmaceutical composition comprising leptin or a leptin mimetic, estrogen and a pharmaceutically acceptable carrier or diluent.

Yet another aspect of this invention is directed to a pharmaceutical composition comprising leptin or a leptin mimetic, a selective estrogen receptor modulator; and a pharmaceutically acceptable carrier or diluent.

Yet another aspect of this invention is directed to a pharmaceutical composition comprising leptin or a leptin mimetic, a bisphosphonate; and a pharmaceutically acceptable carrier or diluent.

Yet another aspect of this invention is directed to a kit comprising:

a. leptin or a leptin mimetic in a first unit dosage form;

b. estrogen in a second unit dosage form; and c. a container.

Yet another aspect of this invention is directed to a kit comprising:

a. leptin or a leptin mimetic in a first unit dosage form;

b. a selective estrogen receptor modulator in a second unit dosage form; and c. a container.

Yet another aspect of this invention is directed to a kit comprising:

a. leptin or a leptin mimetic in a first unit dosage form;

b. a bisphosphonate in a second unit dosage form; and c. a container.

Preferably post-menopausal women and men over the age of 60 are treated.

Leptin and fragments thereof are particularly preferred agents in the pharmaceutical compositions and methods of this invention. Leptin is most particularly preferred.

A preferred dosage is about 0.0001 to 1000 mg/kg/day of leptin or a leptin mimetic. An especially preferred dosage is about 0.001 to 100 mg/kg/day of leptin or a leptin mimetic.

The phrase "condition(s) which presents with low bone mass" refers to a condition where the level of bone mass is below the age specific normal as defined in standards by the World Health Organization "Assessment of Fracture Risk and its Application to Screening for Postmenopausal Osteoporosis (1994). Report of a World Health Organization Study Group. World Health Organization Technical Series 843". Included in "condition(s) which presents with low bone mass" are primary and secondary osteoporosis. Secondary osteoporosis includes glucocorticoid-induced osteoporosis, hyperthyroidism-induced osteoporosis, immobilization-induced osteoporosis, heparin-induced osteoporosis and immunosuppressive-induced osteoporosis. Also included is periodontal disease, alveolar bone loss, osteotomy bone loss and childhood idiopathic bone loss. The "condition(s) which presents with low bone mass" also includes long term complications of osteoporosis such as curvature of the spine, loss of height and prosthetic surgery.

The phrase "condition which presents with low bone mass" also refers to a mammal known to have a significantly higher than average chance of developing such diseases as are described above including osteoporosis (e.g., post-menopausal women, men over the age of 60.

Those skilled in the art will recognize that the term bone mass actually refers to bone mass per unit area which is sometimes (although not strictly correctly) referred to as bone mineral density.

The term "treating", "treat" or "treatment" as used herein includes preventative (e.g., prophylactic), palliative and curative treatment.

The term "leptin mimetic" as used herein means any ligands including recombinant products and small molecules which can bind to and/or activate the leptin receptor (OB-R) and act as receptor agonists. Methods for the recombinant production of leptin have been described by Friedman et al., UK Patent Application No. 2292382.

A fragment of leptin or a leptin fragment is any active portion of the leptin molecule.

By "pharmaceutically acceptable" it is meant the carrier, diluent, excipients, and/or salt must be compatible with the other ingredients of the formulation, and not deleterious to the recipient thereof.

The expression "pharmaceutically-acceptable salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate and 4-toluenesulfonate. The expression also refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methylglucamine), benethamine (N-benzylphenethylamine), piperazine or tromethamine (2-amino-2-hydroxymethyl-1,3-propanediol).

The term "mammal" is meant to include both companion animals and humans. The phrase "companion animal" refers to a household pet or other domesticated animal such as, but not limited to, cattle, sheep, ferrets, swine, horses, poultry, fish, rabbits, goats, dogs, cats and the like. Particularly preferred companion animals are dogs and cats.

The methods of this invention result in bone formation resulting in decreased fracture rates. This invention makes a significant contribution to the art by providing compounds and methods that increase bone formation resulting in prevention, retardation, and/or regression of osteoporosis and related bone disorders.

Other features and advantages of this invention will be apparent from the specification and appendant claims which describe the invention.

DETAILED DESCRIPTION OF THE INVENTION

Leptin is a 16 kiloDalton peptide hormone produced by adipose tissue. Leptin can be prepared according to the methods disclosed in Murakami et al., Biochem Biophys Res Com. 209:944–952. Further, the mouse and human OB genes can be cloned as described in Friedman et al., UK Patent Application No. 2292382 and Zhang et al., Nature, 1994,372:425–431. Leptin receptor, OB-R, can be can be cloned as described in Tartaglia et al., Cell, 1995, 83:1263–1271.

Certain leptin mimetics and leptin fragments may be prepared as described in International Patent Application Publication No. WO97/46585, which is incorporated herein by reference.

Many of the compounds of this invention are acidic and they form a salt with a pharmaceutically acceptable cation. Some of the compounds of this invention are basic and they form a salt with a pharmaceutically acceptable anion. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

The compounds of this invention, prodrugs thereof and pharmaceutically acceptable salts of said compounds and prodrugs are all adapted to therapeutic use as agents that stimulate bone formation and increase bone mass in a vertebrates, e.g., mammals, and particularly humans. Since bone formation is closely related to the development of osteoporosis and bone related disorders, these compounds, prodrugs thereof and pharmaceutically acceptable salts of said compounds and said prodrugs, by virtue of their action on bone, prevent, arrest and/or regress osteoporosis.

The compounds of this invention may be combined with a mammalian selective estrogen receptor modulator. Any selective estrogen receptor modulator may be used as the second compound of this invention. The term selective estrogen receptor modulator refers to compounds which bind with the estrogen receptor, inhibit bone turnover and/or prevent bone loss. A variety of these compounds are described and referenced below. The disclosure of each of the U.S. patents listed below is incorporated herein by reference.

A preferred selective estrogen receptor modulator is droloxifene: (phenol, 3-(1-(4-(2-(dimethylamino)ethoxy) phenyl)-2-phenyl-1-butenyl)-, (E)-) and related compounds which are disclosed in U.S. Pat. No. 5,047,431.

Another preferred selective estrogen receptor modulator is 3-(4-(1,2-diphenyl-but-1-enyl)-phenyl)-acrylic acid, which is disclosed in Willson et al., Endocrinology, 1997, 138, 3901–3911.

Another preferred selective estrogen receptor modulator is tamoxifen: (ethanamine, 2-(4-(1,2-diphenyl-1-butenyl) phenoxy)-N,N-dimethyl, (Z)-2-, 2-hydroxy-1,2,3-propanetricarboxylate(1:1)) and related compounds which are disclosed in U.S. Pat. No. 4,536,516.

Another related compound is 4-hydroxy tamoxifen which is disclosed in U.S. Pat. No. 4,623,660.

A preferred selective estrogen receptor modulator is raloxifene: (methanone, (6-hydroxy-2-(4-hydroxyphenyl) benzo[b]thien-3-yl)(4-(2-(1-piperidinyl)ethoxy)phenyl)-hydrochloride) which is disclosed in U.S. Pat. No. 4,418,068.

Another preferred selective estrogen receptor modulator is toremifene: (ethanamine, 2-(4-(4-chloro-1,2-diphenyl-1-butenyl)phenoxy)-N,N-dimethyl-, (Z)-, 2-hydroxy-1,2,3-propanetricarboxylate (1:1) which is disclosed in U.S. Pat. No. 4,996,225.

Another preferred selective estrogen receptor modulator is centchroman: 1-(2-((4-(-methoxy-2,2, dimethyl-3-phenyl-chroman-4-yl)-phenoxy)-ethyl)-pyrrolidine, which is disclosed in U.S. Pat. No. 3,822,287. Also preferred is levormeloxifene.

Another preferred selective estrogen receptor modulator is idoxifene: (E)-1-(2-(4-(1-(4-iodo-phenyl)-2-phenyl-but-1-enyl)-phenoxy)-ethyl)-pyrrolidinone, which is disclosed in U.S. Pat. No. 4,839,.

Another preferred selective estrogen receptor modulator is 2-(4-methoxyphenyl)-3-[4-(2-piperidin-1-yl-ethoxy)-phenoxy]-benzo[b]thiophen-6-ol which is disclosed in U.S. Pat. No. 5,488,058.

Another preferred selective estrogen receptor modulator is 6-(4-hydroxyphenyl)-5-(4-(2-piperidin-1-yl-ethoxy)-benzyl)-naphthalen-2-ol which is disclosed in U.S. Pat. No. 5,484,795.

Another preferred selective estrogen receptor modulator is (4-(2-(2-azabicyclo[2.2.1]hept-2-yl)-ethoxy)-phenyl)-(6- hydroxy-2-(4-hydroxy-phenyl)-benzo[b]thiophen-3-yl)-methanone which is disclosed, along with methods of preparation, in PCT publication no. WO 95/10513 assigned to Pfizer Inc and designating, inter alia, the United States. The disclosure thereof is incorporated herein by reference.

Other preferred selective estrogen receptor modulators include compounds as described in commonly assigned U.S. Pat. No. 5,552,412, the disclosure of which is incorporated herein by reference. Especially preferred compounds described therein are:

cis-6-(4-fluoro-phenyl)-5-(4-(2-piperidin-1-yl-ethoxy)-phenyl)-5,6,7,8-tetrahydro-naphthalen-2-ol;
(−)-cis-6-phenyl-5-(4-(2-pyrrolidin-1-yl-ethoxy)-phenyl)-5,6,7,8-tetrahydronaphthalen-2-ol;
cis-6-phenyl-5-(4-(2-pyrrolidin-1-yl-ethoxy)-phenyl)-5,6,7,8-tetrahydronaphthalen-2-ol;
cis-1-(6'-pyrrolodinoethoxy-3'-pyridyl)-2-phenyl-6-hydroxy-1,2,3,4-tetrahydronaphthalene;
1-(4'-pyrrolidinoethoxyphenyl)-2-(4"-fluorophenyl)-6-hydroxy-1,2,3,4-tetrahydroisoquinoline;
cis-6-(4-hydroxyphenyl)-5-(4-(2-piperidin-1-yl-ethoxy)-phenyl)-5,6,7,8-tetrahydro-naphthalen-2-ol; and
1-(4'-pyrrolidinolethoxyphenyl)-2-phenyl-6-hydroxy-1,2,3,4-tetrahydroisoquinoline.

Other selective estrogen receptor modulators are described in U.S. Pat. No. 4,133,814, which discloses derivatives of 2-phenyl-3-aroyl-benzothiophene and 2-phenyl-3-aroylbenzothiophene-1-oxide.

The utility of the compounds of the present invention as medical agents in the treatment of conditions which present with low bone mass (e.g., osteoporosis) in a vertebrates, e.g., mammals (e.g. humans, particularly the female) is demonstrated by the activity of the compounds of this invention in conventional assays, including a receptor binding assay, in vivo assays, and a fracture healing assay. A leptin receptor binding assay is described in Tartaglia et al., Cell 83:1263–1271, 1995. The in vivo bone formation assay may be used to determine the activity of the compounds of this invention. The in vivo anti-resorption assay may be used to determine the anti-resorptive activity of the compounds of this invention. The combination and sequential treatment assay described below is useful for demonstrating the utility of the combinations of the bone forming agents (e.g., the compounds of this invention) and anti-resorptive agents (e.g., estrogen agonists/antagonists) described herein. The fracture healing assays described below are useful for demonstrating the utility of the compounds in this invention for enhancing the healing of a bone fracture. Such assays also provide a means whereby the activities of the compounds of this invention (or the other anabolic agents and anti-resorptive agents described herein) can be compared to each other and with the activities of other known compounds. The results of these comparisons are useful for determining dosage levels in a vertebrates, e.g., mammals, including humans, for the treatment of such diseases.

In Vivo Bone Formation Assay

The activity of the compounds in this invention in stimulating bone formation and increasing bone mass can be tested in intact male or female rats, sex hormone deficient male (orchidectomy) or female (ovariectomy) rats.

Male or female rats at different ages (such as 3 months of age) can be used in the study. The rats are either intact or castrated (ovariectomized or orchidectomized), and treated p.o., s.c. or i.p. with a test compound at different doses (such as 1, 3, or 10 mg/kg/day) for 30 days. In the castrated rats, treatment is started at the next day after surgery (for the purpose of preventing bone loss) or at the time bone loss has already occured (for the purpose of restoring bone mass). During the study, all rats are allowed free access to water and a pelleted commercial diet (Teklad Rodent Diet #8064, Harlan Teklad, Madison, Wis.) containing 1.46% calcium, 0.99% phosphorus and 4.96 IU/g of Vitamin $D_3$. All rats are given subcutaneous injections of 10 mg/kg calcein on days 12 and 2 before sacrifice. The rats are sacrificed. The following endpoints are determined:

Femoral Bone Mineral Measurements

The right femur from each rat is removed at autopsy and scanned using dual energy X-ray absorptiometry (DXA, QDR 1000/W, Hologic Inc., Waltham, Mass.) equipped with "Regional High Resolution Scan" software (Hologic Inc., Waltham, Mass.). The scan field size is 5.08×1.902 cm, resolution is 0.0254×0.0127 cm and scan speed is 7.25 mm/second. The femoral scan images are analyzed and bone area, bone mineral content (BMC), and bone mineral density (BMD) of whole femora (WF), distal femoral metaphyses (DFM), femoral shaft (FS), and proximal femora (PF) are determined.

Tibial Bone Histomorphometric Analyses

The right tibia is removed at autopsy, dissected free of muscle, and cut into three parts. The proximal tibia and the tibial shaft are fixed in 70% ethanol, dehydrated in graded concentrations of ethanol, defatted in acetone, then embedded in methyl methacrylate (Eastman Organic Chemicals, Rochester, N.Y.).

Frontal sections of proximal tibial metaphyses at 4 and 10 $\mu$m thickness are cut using a Reichert-Jung Polycut S microtome. The 4 $\mu$m sections are stained with modified Masson's Trichrome stain while the 10 $\mu$m sections remained unstained. One 4 $\mu$m and one 10 $\mu$m section from each rat is used for cancellous bone histomorphometry.

Cross sections of tibial shaft at 10 $\mu$m thickness are cut using a Reichert-Jung Polycut S microtome. These sections are used for cortical bone histomorphometric analysis.

Cancellous bone histomorphometry: A Bioquant OS/2 histomorphometry system (R&M Biometrics, Inc., Nashville, Tenn.) is used for the static and dynamic histomorphometric measurements of the secondary spongiosa of the proximal tibial metaphyses between 1.2 and 3.6 mm distal to the growth plate-epiphyseal junction. The first 1.2 mm of the tibial metaphyseal region needs to be omitted in order to restrict measurements to the secondary spongiosa. The 4 $\mu$m sections are used to determine indices related to bone volume, bone structure, and bone resorption, while the 10 $\mu$m sections are used to determine indices related to bone formation and bone turnover.

I) Measurements and calculations related to trabecular bone volume and structure: (1) Total metaphyseal area (TV, $mm^2$): metaphyseal area between 1.2 and 3.6 mm distal to the growth plate-epiphyseal junction. (2) Trabecular bone area (BV, $mm^2$): total area of trabeculae within TV. (3) Trabecular bone perimeter (BS, mm): the length of total perimeter of trabeculae. (4) Trabecular bone volume (BV/TV, %): BV/TV×100. (5) Trabecular bone number (TBN, #/mm): 1.199/2×BS/TV. (6) Trabecular bone thickness (TBT, $\mu$m): (2000/1.199)×(BV/BS). (7) Trabecular bone separation (TBS, $\mu$m): (2000×1.199)×(TV−BV).

II) Measurements and calculations related to bone resorption: (1) Osteoclast number (OCN, #): total number of osteoclast within total metaphyseal area. (2) Osteoclast perimeter (OCP, mm): length of trabecular perimeter covered by osteoclast. (3) Osteoclast number/mm (OCN/mm,

/mm): OCN/BS. (4) Percent osteoclast perimeter (%OCP, %): OCP/BS×100.

III) Measurements and calculations related to bone formation and turnover: (1) Single-calcein labeled perimeter (SLS, mm): total length of trabecular perimeter labeled with one calcein label. (2) Double-calcein labeled perimeter (DLS, mm): total length of trabecular perimeter labeled with two calcein labels. (3) Inter-labeled width (ILW, $\mu$m): average distance between two calcein labels. (4) Percent mineralizing perimeter (PMS, %): (SLS/2+DLS)/BS×100. (5) Mineral apposition rate (MAR, $\mu$m/day): ILW/label interval. (6) Bone formation rate/surface ref. (BFR/BS, $\mu m^2/d/\mu m$): (SLS/2+DLS)×MAR/BS. (7) Bone turnover rate (BTR, %/y): (SLS/2+DLS)×MAR/BV×100.

Cortical bone histomorphometry: A Bioquant OS/2 histomorphometry system (R&M Biometrics, Inc., Nashville, Tenn.) is used for the static and dynamic histomorphometric measurements of tibial shaft cortical bone. Total tissue area, marrow cavity area, periosteal perimeter, endocortical perimeter, single labeled perimeter, double labeled perimeter, and interlabeled width on both periosteal and endocortical surface are measured, and cortical bone area (total tissue area—marrow cavity area), percent cortical bone area (cortical area/total tissue area×100), percent marrow area (marrow cavity area/total tissue area×100), periosteal and endocortical percent labeled perimeter [(single labeled perimeter/2+double labeled perimeter)/total perimeter×100], mineral apposition rate (interlabeled width/intervals), and bone formation rate [mineral apposition rate× [(single labeled perimeter/2+double labeled perimeter)/total perimeter] are calculated.

Statistics

Statistics can be calculated using StatView 4.0 packages (Abacus Concepts, Inc., Berkeley, Calif.). The analysis of variance (ANOVA) test followed by Fisher's PLSD (Stat View, Abacus Concepts Inc., 1918 Bonita Ave, Berkeley, Calif. 94704-1014) is used to compare the differences between groups.

Fracture Healing Assays

Assay for Effects on Fracture Healing After Systemic Administration

Fracture Technique: Sprage-Dawley rats at 3 months of age are anesthetized with Ketamine. A 1 cm incision is made on the anteromedial aspect of the proximal part of the right tibia or femur. The following describes the tibial surgical technique. The incision is carried through to the bone, and a 1 mm hole is drilled 4 mm proximal to the distal aspect of the tibial tuberosity 2 mm medial to the anterior ridge. Intramedullary nailing is performed with a 0.8 mm stainless steel tube (maximum load 36.3 N, maximum stiffness 61.8 N/mm, tested under the same conditions as the bones). No reaming of the medullary canal is performed. A standardized closed fracture is produced 2 mm above the tibiofibular junction by three-point bending using specially designed adjustable forceps with blunt jaws. To minimize soft tissue damage, care is taken not to displace the fracture. The skin is closed with monofilament nylon sutures. The operation is performed under sterile conditions. Radiographs of all fractures are taken immediately after nailing, and rats with fractures outside the specified diaphyseal area or with displaced nails are excluded. The remaining animals are divided randomly into the following groups with 10–12 animals per each subgroup per time point for testing the fracture healing. The first group receives daily gavage of vehicle (water: 100% Ethnanol=95:5) at 1 ml/rat, while the others receive daily gavage from 0.01 to 100 mg/kg/day of the compound or compounds to be tested (1 ml/rat) for 10, 20, 40 and 80 days.

At 10, 20, 40 and 80 days, 10–12 rats from each group are anesthetized with Ketamine and sacrificed by exsanguination. Both tibiofibular bones are removed by dissection and all soft tissue is stripped. Bones from 5–6 rats for each group are stored in 70% ethanol for histological analysis, and bones from another 5–6 rats for each group are stored in Ringer's solution (+4° C., pH 7.4) for radiographs and biomechanical testing which is performed.

Histological Analysis: The methods for histologic analysis of fractured bone have been previously published by Mosekilde and Bak (The Effects of Growth Hormone on Fracture Healing in Rats: A Histological Description. Bone, 14:19–27, 1993). Briefly, the fracture side is sawed 8 mm to each side of the fracture line, embedded undecalcified in methymethacrylate, and cut frontals sections on a Reichert-Jung Polycut microtome in 8 $\mu$m thick. Masson-Trichrome stained mid-frontal sections (including both tibia and fibula) are used for visualization of the cellullar and tissue response to fracture healing with and without treatment. Sirius red stained sections are used to demonstrate the characterisitics of the callus structure and to differentiate between woven bone and lamellar bone at the fracture site. The following measurements are performed: (1) fracture gap—measured as the shortest distance between the cortical bone ends in the fracture, (2) callus length and callus diameter, (3) total bone volume area of callus, (4) bony tissue per tissue area inside the callus area, (5) fibrous tissue in the callus, and (6) cartilage area in the callus.

Biomechanical Analysis: The methods for biomechanical analysis have been previously published by Bak and Andreassen (The Effects of Aging on Fracture Healing in Rats. Calcif Tissue Int 45:292–297,1989). Briefly, radiographs of all fractures are taken prior to the biomechanical test. The mechanical properties of the healing fractures are analyzed by a destructive three- or four-point bending procedure. Maximum load, stiffness, energy at maximum load, deflection at maximum load, and maximum stress are determined.

Assay for Effects on Fracture Healing After Local Administration

Fracture Technique: Female or male beagle dogs at approximately 2 years of age are used under anesthesia in the study. Transverse radial fractures are produced by slow continuous loading in three-point bending as described by Lenehan et al. (Lenehan, T. M.; Balligand, M.; Nunamaker, D. M.; Wood, F. E.: Effects of EHDP on Fracture Healing in Dogs. J Orthop Res 3:499–507; 1985). The wire is pulled through the fracture site to ensure complete anatomical disruption of the bone. Thereafter, local delivery of the compound or compounds being tested to the fracture site is achieved by slow release of compound(s) delivered by slow release pellets or by administration of the compound(s) in a suitable formulation such as a paste gel solution or suspension for 10, 15, or 20 weeks.

Histological Analysis: The methods for histologic analysis of fractured bone have been previously published by Peter et al. (Peter, C. P.; Cook, W. O.; Nunamaker, D. M.; Provost, M. T.; Seedor, J. G.; Rodan, G. A. Effects of alendronate on fracture healing and bone remodeling in dogs. J. Orthop. Res. 14:74–70,1996) and Mosekilde and Bak (The Effects of Growth Hormone on Fracture Healing in Rats: A Histological Description. Bone, 14:19–27, 1993).

Briefly, after sacrifice, the fracture side is sawed 3 cm to each side of the fracture line, embedded undecalcified in methymethacrylate, and cut on a Reichert-Jung Polycut microtome into 8 μm thick frontal sections. Masson-Trichrome stained mid-frontal sections (including both tibia and fibula) are used for visualization of the cellullar and tissue response to fracture healing with and without treatment. Sirius red stained sections are used to demonstrate the characterisitics of the callus structure and to differentiate between woven bone and lamellar bone at the fracture site. The following measurements are performed: (1) fracture gap—measured as the shortest distance between the cortical bone ends in the fracture, (2) callus length and callus diameter, (3) total bone volume area of callus, (4) bony tissue per tissue area inside the callus area, (5) fibrous tissue in the callus and (6) cartilage area in the callus.

Biomechanical Analysis: The methods for biomechanical analysis have been previously published by Bak and Andreassen (The Effects of Aging on Fracture Healing in Rats. Calcif Tissue Int 45:292–297, 1989) and Peter et al. (Peter, C. P.; Cook, W. O.; Nunamaker, D. M.; Provost, M. T.; Seedor, J. G.; Rodan, G. A. Effects of Alendronate On Fracture Healing And Bone Remodeling In Dogs. J. Orthop. Res. 14:74–70, 1996). Briefly, radiographs of all fractures are taken prior to the biomechanical test. The mechanical properties of the healing fractures are analyzed by a destructive three- or four-point bending procedures. Maximum load, stiffness, energy at maximum load, deflection at maximum load, and maximum stress are determined.

In Vivo Anti-resorption Assay

Anti-resorptive agents are a class of compounds which inhibit bone turnover and prevent bone loss. The ovariectomized rat bone loss model has been widely used as a model of postmenopausal bone loss. Using this model, one can test the efficacy of the compounds of this invention in preventing bone loss and inhibiting bone resorption.

Sprague-Dawley female rats (Charles River, Wilmington, Mass.) at different ages (such as 5 months of age) are used in these studies. The rats are singly housed in 20 cm×32 cm×20 cm cages during the experimental period. All rats are allowed free access to water and a pelleted commercial diet (Agway ProLab 3000, Agway County Food, Inc., Syracuse, N.Y.) containing 0.97% calcium, 0.85% phosphorus, and 1.05 IU/g of Vitamin $D_3$.

A group of rats (8 to 10) are sham-operated and treated p.o. with vehicle (10% ethanol and 90% saline, 1 ml/day), while the remaining rats are bilaterally ovariectomized (OVX) and treated with either vehicle or with a test compound or compounds of this invention at different doses (such as 5, 10, or 20 mg/kg, daily p.o., s.c. or i.p.) for a certain period (such as 4 weeks). All rats are given subcutaneous injections of 10 mg/kg calcein (fluorochrome bone marker) 12 and 2 days before being sacrificed in order to examine the dynamic changes in bone tissue. After 4 weeks of treatment, the rats are sacrificed and autopsied. The following endpoints are determined:

Body Weight Gain: Body weight at autopsy minus body weight at surgery.

Total Serum Cholesterol: Blood is obtained by cardiac puncture and allowed to clot at 4° C., and then centrifuged at 2,000 g for 10 min. Serum samples are analyzed for total serum cholesterol using a high performance cholesterol calorimetric assay (Boehringer Mannheim Biochemicals, Indianapolis, Ind.).

Femoral Bone Mineral Measurements: The right femur from each rat is removed at autopsy and scanned using dual energy X-ray absorptiometry (DEXA, QDR 1000/W, Hologic Inc., Waltham, Mass.) equipped with "Regional High Resolution Scan" software (Hologic Inc., Waltham, Mass.). The scan field size is 5.08×1.902 cm, resolution is 0.0254×0.0127 cm and scan speed is 7.25 mm/second. The femoral scan images are analyzed and bone area, bone mineral content (BMC), and bone mineral density (BMD) of whole femora (WF), distal femoral metaphyses (DFM), femoral shaft (FS), and proximal femora (PF) are determined.

Proximal Tibial Metaphyseal Cancellous Bone Histomorphometric Analyses: The right tibia is removed at autopsy, dissected free of muscle, and cut into three parts. The proximal tibia is fixed in 70% ethanol, dehydrated in graded concentrations of ethanol, defatted in acetone, then embedded in methyl methacrylate (Eastman Organic Chemicals, Rochester, N.Y.). Frontal sections of proximal tibial metaphyses at 4 and 10 μm thickness are cut using a Reichert-Jung Polycut S microtome. One 4 μm and one 10 μm section from each rat is used for cancellous bone histomorphometry. The 4 μm sections are stained with modified Masson's Trichrome stain while the 10 μm sections remained unstained.

A Bioquant OS/2 histomorphometry system (R&M Biometrics, Inc., Nashville, Tenn.) is used for the static and dynamic histomorphometric measurements of the secondary spongiosa of the proximal tibial metaphyses between 1.2 and 3.6 mm distal to the growth plate-epiphyseal junction. The first 1.2 mm of the tibial metaphyseal region is omitted in order to restrict measurements to the secondary spongiosa. The 4 μm sections are used to determine indices related to bone volume, bone structure, and bone resorption, while the 10 μm sections are used to determine indices related to bone formation and bone turnover.

I. Measurements and Calculations Related to Trabecular Bone Volume and Structure
 1. Total metaphyseal area (TV, $mm^2$): metaphyseal area between 1.2 and 3.6 mm distal to the growth plate-epiphyseal junction.
 2. Trabecular bone area (BV, $mm^2$): total area of trabeculae within TV.
 3. Trabecular bone perimeter (BS, mm): the length of total perimeter of trabeculae.
 4. Trabecular bone volume (BV/TV, %): BV/TV×100.
 5. Trabecular bone number (TBN, #/mm): 1.199/2×BS/TV.
 6. Trabecular bone thickness (TBT, μm): (2000/1.199)×(BV/BS).
 7. Trabecular bone separation (TBS, μm): (2000×1.199)×(TV−BV).

II. Measurements and Calculations Related to Bone Resorption
 1. Osteoclast number (OCN, #): total number of osteoclast within total metaphyseal area.
 2. Osteoclast perimeter (OCP, mm): length of trabecular perimeter covered by osteoclast.
 3. Osteoclast number/mm (OCN/mm, #/mm): OCN/BS.
 4. Percent osteoclast perimeter (%OCP, %): OCP/BS×100.

III. Measurements and Calculations Related to Bone Formation and Turnover
 1. Single-calcein labeled perimeter (SLS, mm): total length of trabecular perimeter labeled with one calcein label.
 2. Double-calcein labeled perimeter (DLS, mm): total length of trabecular perimeter labeled with two calcein labels.

3. Inter-labeled width (ILW, μm): average distance between two calcein labels.
4. Percent mineralizing perimeter (PMS, %): (SLS/2+DLS)/BS×100.
5. Mineral apposition rate (MAR, μm/day): ILW/label interval.
6. Bone formation rate/surface ref. (BFR/BS, $\mu m^2/d/\mu m$): (SLS/2+DLS)×MAR/BS.
7. Bone turnover rate (BTR, %/y): (SLS/2+DLS)×MAR/BV×100.

Statistics

Statistics are calculated using StatView 4.0 packages (Abacus Concepts, Inc., Berkeley, Calif.). The analysis of variance (ANOVA) test followed by Fisher's PLSD (Stat View, Abacus Concepts Inc. 1918 Bonita Ave, Berkeley, Calif. 94704-1014) is used to compare the differences between groups.

Combination and Sequential Treatment Assay

The following protocols can of course be varied by those skilled in the art. For example, intact male or female rats, sex hormone deficient male (orchidectomy) or female (ovariectomy) rats may be used. In addition, male or female rats at different ages (such as 12 months of age) can be used in the studies. The rats can be either intact or castrated (ovariectomized or orchidectomized), and a compound or compounds of this invention are adminstered at different doses (such as 0.1 to 10 mg/kg/day) for a certain period (such as two weeks to two months), and followed by administration of an anti-resorptive agent at different doses (such as 0.1 to 10 mg/kg/day) for a certain period (such as two weeks to two months), or a combination treatment with both anabolic agent and anti-resorptive agent at different doses for a certain period (such as two weeks to two months). In the castrated rats, treatment can be started on the next day after surgery (for the purpose of preventing bone loss) or at the time bone loss has already occurred (for the purpose of restoring bone mass).

The rats are sacrificed under ketamine anesthesia. The following endpoints are determined:

Femoral bone mineral measurements are performed as described above in the protocol for the in vivo antiresorption assay.

Lumbar Vertebral Bone Mineral Measurements: Dual energy X-ray absorptiometry (QDR 1000/W, Hologic, Inc., Waltham, Mass.) equipped with a "Regional High Resolution Scan" software (Hologic, Inc., Waltham, Mass.) is used to determined the bone area, bone mineral content (BMC), and bone mineral density (BMD) of whole lumbar spine and each of the six lumbar vertebrae (LV1–6) in the anesthetized rats. The rats are anesthetized by injection (i.p.) of 1 ml/kg of a mixture of ketamine/rompun (ratio of 4 to 3), and then placed on a rat platform. The scan field sized is 6×1.9 cm, resolution is 0.0254×0.0127 cm, and scan speed is 7.25 mm/sec. The whole lumbar spine scan image is obtained and analyzed. Bone area (BA), and bone mineral content (BMC) is determined, and bone mineral density is calculated (MBC divided by BA) for the whole lumbar spine and each of the six lumbar vertebrae (LV1–6).

Proximal tibial metaphyseal cancellous bone histomorphometric analyses are performed as described above above in the protocol for the in vivo antiresorption assay.

Measurements and calculations related to trabecular bone volume and structure, bone resorption, and bone formation and turnover are performed as described above above in the protocol for the in vivo antiresorption assay. Further, the data thus obtained is analyzed using the statistical manipulations described above above in the protocol for the in vivo antiresorption assay.

Administration of leptin for four weeks increased femur length by 6% and increased cortical bone volumetric content by 18%, as determined by peripheral quantitative computerized tomography. Bone volumetric density was unchanged, suggesting that leptin-induced bone was normal. These results show that stature of the ob/ob mouse is due to a developmental defect and is reversible upon administration of leptin or a leptin mimetic.

Administration of the compounds of this invention can be via any method which delivers a compound of this invention systemically and/or locally (e.g., at the site of the bone fracture, osteotomy, or orthopedic surgery. These methods include oral routes, parenteral routes, intraduodenal routes, etc. Generally, the compounds of this invention are administered orally, but parenteral administration (e.g., intravenous, intramuscular, subcutaneous or intramedullary or on sites of bone fracture) may be utilized, for example, where oral administration is inappropriate for the instant target or where the patient is unable to ingest the drug.

The compounds are used for the treatment and promotion of healing of bone fractures and osteotomies by the local application (e.g., to the sites of bone fractures of osteotomies) of the compounds of this invention or compositions thereof. The compounds of this invention are applied to the sites of bone fractures or osteotomies, for example, either by injection of the compound in a suitable solvent (e.g., an oily solvent such as arachis oil) to the cartilage growth plate or, in cases of open surgery, by local application thereto of such compounds in a suitable carrier such as bone-wax, demineralized bone powder, polymeric bone cements, bone sealants etc. Alternatively, local application can be achieved by applying a solution or dispersion of the compound in a suitable carrier onto the surface of, or incorporating it into solid or semi-solid implants conventionally used in orthopedic surgery, such as dacron-mesh, gel-foam and kiel bone, or prostheses.

Two different compounds of this invention can be co-administered simultaneously or sequentially in any order, or a single pharmaceutical composition comprising, for example, leptin or a leptin mimetic and a second compound as described above in a pharmaceutically acceptable carrier can be administered.

In any event the amount and timing of a compound administered will, of course, be dependent on the subject being treated, on the severity of the affliction, on the manner of administration and on the judgement of the prescribing physician. Thus, because of patient to patient variability, the dosages given below are a guideline and the physician may titrate doses of the compound to achieve the treatment (e.g., bone mass augmentation or bone loss prevention) that the physician considers appropriate for the patient. In considering the degree of treatment desired, the physician must balance a variety of factors such as bone mass starting level, age of the patient, presence of preexisting disease, as well as presence of other diseases (e.g., cardiovascular).

In general an amount of a compound or compounds of this invention is used that is sufficient to augment bone mass to a level which is above the bone fracture threshold (as detailed in the World Health Organization Study previously cited herein).

In general an effective dosage for the leptin or leptin mimetic described above is in the range of 0.0001 to 1000 mg/kg/day, preferably 0.001 to 100 mg/kg/day.

The compounds of the present invention are generally administered in the form of a pharmaceutical composition comprising at least one of the compounds of this invention together with a pharmaceutically acceptable carrier or diluent. Thus, the compounds of this invention can be administered individually or together in any conventional oral, parenteral, rectal or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g.,topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences,* Mack Publishing Company, Easton, Pa., 18th Edition (1990).

Pharmaceutical compositions according to this invention may contain 0.1%–95% of the compound(s) of this invention, preferably 1%–70%. In any event, the composition or formulation to be administered will contain a quantity of a compound(s) according to this invention in an amount effective to treat the disease/condition of the subject being treated, e.g., a bone disorder.

Since the present invention has an aspect that relates to the augmentation and maintenance of bone mass by treatment with a combination of active ingredients which may be administered separately, the invention also relates to combining separate pharmaceutical compositions in kit form. The kit comprises two separate pharmaceutical compositions: leptin or a leptin mimetic, a prodrug thereof or a pharmaceutically acceptable salt of said compound or said prodrug and a second compound as described above. The kit comprises a container for containing the separate compositions such as a divided bottle or a divided foil packet, however, the separate compositions may also be contained within a single, undivided container. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the dosage form so specified should be ingested. Another example of such a memory aid is a calendar printed on the card e.g., as follows "First Week, Monday, Tuesday, . . . etc . . . Second Week, Monday, Tuesday, . . . " etc. Other variations of memory aids will be readily apparent. A "daily dose" can be a single tablet or capsule or several tablets or capsules to be taken on a given day. Also, a daily dose of leptin or a leptin mimetic, a prodrug thereof or a pharmaceutically acceptable salt of said compound or said prodrug can consist of one tablet or capsule while a daily dose of the second compound can consist of several tablets or capsules and vice versa. The memory aid should reflect this.

It should be understood that the invention is not limited to the particular embodiments described herein, but that various changes and modifications may be made without departing from the spirit and scope of this novel concept as defined by the following claims.

What is claimed is:

1. A method for augmenting bone mass and preventing bone loss in a mammal in need thereof comprising administering to said mammal a therapeutically effective amount of a combination of 1) leptin, a fragment thereof or a leptin mimetic, and 2) estrogen.

2. A method for augmenting bone mass and preventing bone loss in a mammal in need thereof comprising administering to said mammal a therapeutically effective amount of a combination of 1) leptin, a fragment thereof or a leptin mimetic, and 2) a selective estrogen receptor modulator.

3. A method of claim 2 wherein leptin or a fragment thereof is adminstered.

4. A method of claim 3 wherein said selective estrogen receptor modulator is droloxifene.

5. A method of claim 3 wherein said selective estrogen receptor modulator is raloxifene.

6. A method of claim 3 wherein said selective estrogen receptor modulator is idoxifene.

7. A method of claim 3 wherein said selective estrogen receptor modulator is (−)-cis-6-phenyl-5-(4-(2-pyrrolidin-1-yl)-ethoxy)-phenyl)-5,6,7,8-tetrahydronaphthalen-2-ol.

8. A method for augmenting bone mass and preventing bone loss in a mammal in need thereof comprising administering to said mammal a therapeutically effective amount of a combination of 1) leptin, a fragment thereof or a leptin mimetic, and 2) a bisphosphonate.

9. A method of claim 8 wherein leptin or a fragment thereof is administered.

10. A method of claim 9 wherein said bisphosphonate is alendronate.

11. A method of claim 9 wherein said bisphosphonate is risedronate.

12. A method for enhancing bone healing following facial reconstruction, maxillary reconstruction or mandibular reconstruction, enhancing long bone extension, enhancing the healing rate of a bone graft, enhancing prosthetic ingrowth or inducing vertebral synostosis in a mammal comprising administering to said mammal a therapeutically effective amount of leptin, a fragment thereof or a leptin mimetic, and estrogen.

13. A method of claim 12 wherein leptin or a fragment thereof is adminstered.

14. A method for enhancing bone healing following facial reconstruction, maxillary reconstruction or mandibular reconstruction, enhancing long bone extension, enhancing the healing rate of a bone graft, enhancing prosthetic ingrowth or inducing vertebral synostosis in a mammal comprising administering to said mammal a therapeutically effective amount of leptin, a fragment thereof or a leptin mimetic, and a selective estrogen receptor modulator.

15. A method of claim 14 wherein leptin or a fragment thereof is adminstered.

16. A method for enhancing bone healing following facial reconstruction, maxillary reconstruction or mandibular reconstruction, enhancing long bone extension, enhancing the healing rate of a bone graft, enhancing prosthetic ingrowth or inducing vertebral synostosis in a mammal comprising administering to said mammal a therapeutically effective amount of leptin, a fragment thereof or a leptin mimetic, and a bisphosphonate.

17. A method of claim 16 wherein leptin or a fragment thereof is administered.

* * * * *